US00PP34945P2

(12) United States Plant Patent
Bozanic Tanjga

(10) Patent No.: US PP34,945 P2
(45) Date of Patent: Jan. 31, 2023

(54) SHRUB ROSE PLANT NAMED 'BOZFRA021'

(50) Latin Name: *Rosa hybrida*
Varietal Denomination: BOZFRA021

(71) Applicant: Biljana Bozanic Tanjga, Novi Sad (RS)

(72) Inventor: Biljana Bozanic Tanjga, Novi Sad (RS)

(73) Assignee: Pheno Geno Roses B.V.

( * ) Notice: Subject to any disclaimer, the term of this patent is extended or adjusted under 35 U.S.C. 154(b) by 0 days.

(21) Appl. No.: 17/736,569

(22) Filed: May 4, 2022

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./107, 137, 148
CPC ... A01H 5/02; A01H 5/00; A01H 6/74; A01H 6/749
See application file for complete search history.

(56) References Cited

PUBLICATIONS

Otto & Sons Nursery Rose List 2022 Availability as of Apr. 9, 2022, retrieved on Jun. 9, 2022 at https://ottoandsonsnursery.com/wp-content/uploads/2022/04/Otto.Rose_.Availability.4.9.22.pdf, pp. 1-6. (Year: 2022).*

Spring Meadow Nursery Flowering Shrubs Starter Plants Catalog and Shrub Reference 2021-2022, retrieved on Jun. 9, 2022 at https://cdn.coverstand.com/65723/717743/fd338d123923398b32713a713f760f32e02147ea.pdf, pp. 1-2, 99. (Year: 2022).*

* cited by examiner

*Primary Examiner* — June Hwu
(74) *Attorney, Agent, or Firm* — Cassandra Bright

(57) ABSTRACT

A new and distinct cultivar of *Rosa* plant named 'BOZFRA021' is disclosed, characterized by fragrant, pink double flowers that bloom profusely from May to September. Plants are tolerant of powdery mildew and black spot. The new variety is a *Rosa*, normally produced as an outdoor garden or container plant.

2 Drawing Sheets

Figure 1:
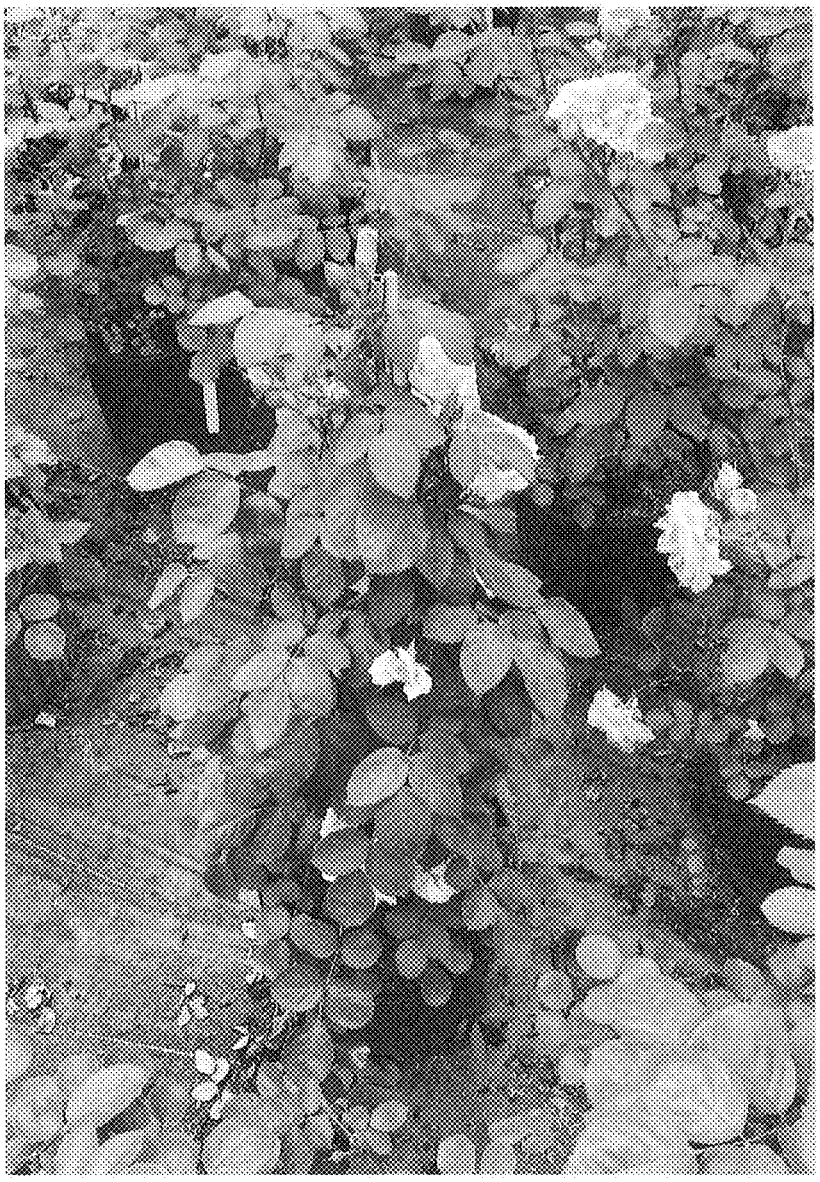

Latin name of the genus and species: *Rosa hybrida.*
Variety denomination: 'BOZFRA021'.

BACKGROUND OF THE INVENTION

The new *Rosa* cultivar is a product of a planned breeding program conducted by the inventor, Biljana Bozanic Tanjga, in Temerin, Serbia. The objective of the breeding program was to produce new profusely flowering shrub rose plants with good disease resistance, and large, vibrantly colored blooms. The cross resulting in this new variety was made during May of 2010.

The seed parent is an unnamed, unpatented proprietary seedling. The pollen parent is a different unnamed, unpatented proprietary seedling. The new variety was discovered in June of 2011 by the inventor in a group of seedlings resulting from the 2010 crossing, in a research nursery in Temerin, Serbia.

Asexual reproduction of the new cultivar was performed by softwood cuttings at a research nursery in Mali Idjos, Serbia in 2012, and has shown that the unique features of this cultivar are stable and reproduced true to type in multiple successive generations.

SUMMARY OF THE INVENTION

The cultivar *Rosa* 'BOZFRA021' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BOZFRA021'. These characteristics in combination distinguish 'BOZFRA021' as a new and distinct *Rosa* cultivar:

1. Medium pink petal color.
2. Double flowers with a rounded shape, and a flat profile of lower and upper parts.
3. Profuse blooming from May to September.
4. Light, sweet fragrance.
5. Tolerant to powdery mildew and black spot.

Plants of the new cultivar 'BOZFRA021' are similar to plants of the seed parent in most horticultural characteristics, however, plants of the new cultivar 'BOZFRA021' differ in the following;

1. The new variety is a shrub, while the seed parent is a climbing plant.
2. Flower color of the new variety is medium pink, while the flower color of the seed parent is light pink.
3. Flowers of the new variety are more fragrant than flowers of the seed parent.
4. Lower flower profile of the new variety is flat. Lower flower profile of the seed parent is concave.

Plants of the new cultivar 'BOZFRA021' are similar to plants of the pollen parent in most horticultural characteristics, however, plants of the new cultivar 'BOZFRA021' differ in the following:

1. The new variety is a shrub, while the pollen parent is a floribunda.

2. Flower color of the new variety is medium pink, while the flower color of the pollen parent is deep pink.
3. Flowers of the new variety are more fragrant than flowers of the pollen parent.

COMMERCIAL COMPARISON

Plants of the new cultivar 'BOZFRA021' are comparable to the patented commercial variety *Rosa* 'Ausboard', U.S. Plant Pat. No. 7,220. The two *Rosa* varieties are similar in most horticultural characteristics; however, the new variety 'BOZFRA021' differs in the following:

1. Flowers of the new variety are a lighter pink than flowers of this comparator.
2. Anthers of the new variety are visible through the petals, while anthers of this comparator are often occluded by the petals.

BRIEF DESCRIPTION OF THE PHOTOGRAPHS

The accompanying photograph in FIG. 1 illustrates in full color a typical plant of 'BOZFRA021' grown in a 2-gallon container. Age of the plant photographed is approximately 5 months.

Figure 2:
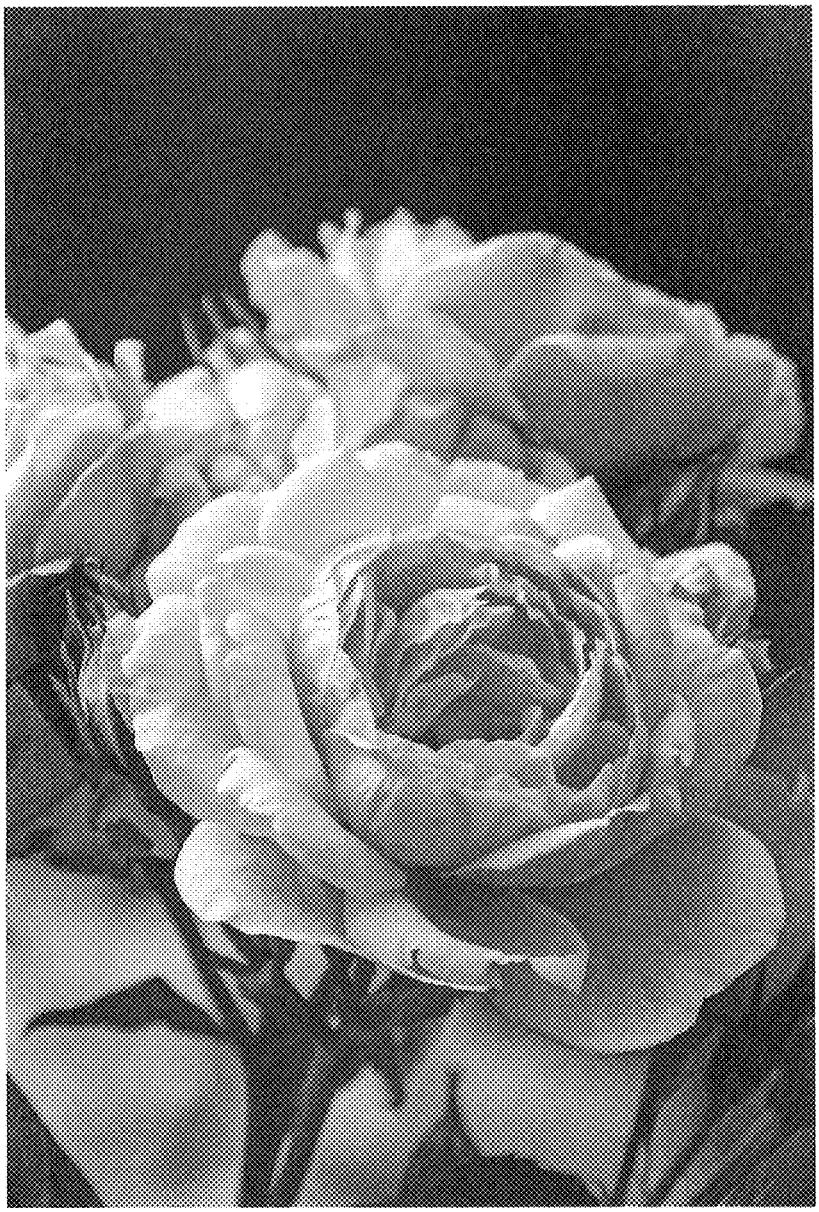

FIG. 2 illustrates a close-up view of flowers of 'BOZFRA021'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BOZFRA021' plants grown outdoors during the Spring and Summer, in Grand Haven, Mich. The growing temperature ranged from 15° C. to 40° C. during the day and from −25° C. to at least 30° C. during the night. General light conditions were bright, normal sunlight. No chemical treatments were used. Measurements and numerical values represent averages of typical plant types.

Botanical classification: *Rosa hybrida* 'BOZFRA021'.

PROPAGATION

Propagation method: Softwood cuttings.
Time to initiate roots: 30 days at 20° C. in summer.
Time to produce rooted plant: 120 days at 20° C. in summer.
Root description: Good density, moderately branched, medium thickness, fibrous, and fleshy. White in color, not accurately measured using R.H.S. chart.

PLANT

Age of plant described: Approximately 2 years old.
Plant type: Perennial shrub.
Rootstock: Own roots.
Growth habit: Upwards and slightly outwards.
Plant shape: Upright.
Height: 85 cm.
Plant spread: 70 cm.
Growth rate: Moderate.
Branching characteristics: Basal.
Length of primary lateral branches: 70 cm.
Diameter of lateral branches: 5 mm.
Quantity of lateral branches: 15.
Internode length: 4 cm.
Stem:
- *Shape*.—Round.
- *Aspect*.—Upright.
- *Strength*.—Strong.
- *Color*.—RHS Yellow-Green 144A.
- *Pubescence*.—None.
- *Anthocyanin on young growth*.—Not present.

Thorns:
- *Quantity*.—3 to 4 per linear cm.
- *Shape*.—Narrow, angled slightly downward.
- *Apex*.—Acicular.
- *Base*.—Obtuse.
- *Height*.—1 cm.
- *Color, immature*.—RHS Greyed-Red 182B.
- *Color, mature*.—RHS Greyed-Red 182B.

FOLIAGE

Leaf:
- *Arrangement*.—Alternate.
- *Quantity*.—10 to 12 per lateral branch.
- *Length*.—13 cm.
- *Width*.—8.5 cm.

Leaflet:
- *Quantity*.—3 to 7 per leaf.
- *Terminal length*.—5 cm.
- *Terminal width*.—4 cm.
- *Lateral length*.—4 cm.
- *Lateral width*.—3 cm.
- *Shape of blade*.—Elliptic.
- *Apex*.—Acute.
- *Base*.—Obtuse.
- *Margin*.—Serrulate. Very weak to no undulation.
- *Texture*.—Smooth and somewhat waxy upper surface. Smooth lower surface.
- *Pubescence*.—None.
- *Appearance*.—Matte upper and lower surfaces.
- *Color*.—Young foliage upper side: RHS Yellow-Green 148A. Young foliage under side: RHS Greyed-Orange 177A. Mature foliage upper side: RHS Green NN137B. Mature foliage under side: RHS Yellow-Green 147B.
- *Venation*.—Type: Pinnate. Venation color upper side: RHS Yellow-Green N144B. Venation color under side: RHS Yellow-Green N144B.

Petiole:
- *Leaf*.—Length: 8 cm. Diameter: 2 mm. Color, upper surface: RHS Yellow-Green 144A, with tinges of Greyed-Purple 184B. Color, lower surface: RHS Yellow-Green 144A. Texture: Smooth on top, with small thorns running the length underneath.
- *Leaflet*.—Length: 2 mm. Diameter: 1 mm. Color, upper surface: RHS Yellow-Green 144A, with tinges of Greyed-Purple 184B. Color, lower surface: RHS Yellow-Green 144A. Texture: Smooth.

Stipules:
- *Quantity*.—2.
- *Shape*.—Linear to acicular.
- *Apex*.—Acicular.
- *Base*.—Fused along petiole.
- *Margin*.—Ciliate.

*Length.*—1.5 cm.
*Width.*—2 mm.
*Texture.*—Smooth, both surfaces.
*Color, upper surface.*—RHS Green NN137B.
*Color, lower surface.*—RHS Yellow-Green 147B.

FLOWER

Natural flowering season: Spring through summer.
Flower type and habit: Terminal cymes of 5 to 10 flowers on lateral branches.
Flower form: Double flower, whorled.
*Shape.*—Round whorl.
*Diameter.*—9 cm.
*Depth.*—4 cm.
*Aspect.*—Upright.
*Persistent or self-cleaning.*—Self-cleaning.
Bud:
*Shape.*—Ovate.
*Length.*—1.5 cm.
*Diameter.*—1 cm.
*Color.*—RHS Yellow-Green N144C.
Petals:
*Arrangement.*—Double whorl.
*Appearance.*—Recurved/slightly cupped petals with notched tips.
*Length.*—Outer whorl: 5 cm. Inner whorl: 3.5 cm.
*Width.*—Outer whorl: 4 cm. Inner whorl: 2 cm.
*Shape.*—Outer whorl: Orbicular/obovate. Inner whorl: Oblong.
*Margin.*—Entire to slightly crenate.
*Apex.*—Obtuse to retuse.
*Fused.*—No.
*Quantity.*—About 70.
*Texture.*—Silky and smooth.
*Color.*—When opening: Upper surface: RHS Red-Purple 65C, some Yellow 8C at base. Lower surface: RHS Greyed-Purple 186D, some Yellow 8C at base. Fully opened: Upper surface: RHS Red-Purple 65C, some Yellow 8C at base. Lower surface: RHS Red-Purple 65C, some Yellow 8C at base.
Petaloids:
*Shape.*—Irregular, folded, and crescent-shaped.
*Arrangement.*—Whorled.
*Quantity.*—15 to 20.
*Margin.*—Slightly crenate.
*Length.*—2 cm.
*Width.*—7 mm.
*Color.*—Immature: RHS Red-Purple 65C, some Yellow 8C at base. Mature: RHS Red-Purple 65C, some Yellow 8C at base.
Sepals:
*Appearance.*—Rough-textured, recurved toward stem.
*Arrangement.*—Whorl around base.
*Quantity.*—5.
*Shape.*—Triangular.
*Margin.*—Entire.
*Sepal extensions.*—Medium.
*Apex.*—Aristate.
*Base.*—Fused.
*Length.*—2.5 cm.
*Width.*—1 cm.
*Texture.*—Rough and somewhat pubescent, especially on upper side.
*Color.*—Immature, upper side: RHS Yellow-Green N144C, with White 155A pubescence. Immature, under side: RHS Yellow-Green N144C. Mature, upper side: RHS Yellow-Green N144C, with White 155A pubescence. Mature, under side: RHS Yellow-Green N144C.
Calyx:
*Shape.*—Collar-like with recurved sepals arranged in a whorl.
*Length.*—2 cm.
*Diameter.*—1.5 cm.
Peduncle:
*Length.*—1.5 cm.
*Diameter.*—2 mm.
*Angle.*—Upright, 75 to 90°.
*Strength.*—Strong.
*Texture.*—Slightly prickly.
*Color.*—RHS Yellow-Green 144A, with tinges of Greyed-Purple 184B sometimes present.
Fragrance: Lightly fragrant and sweet.

REPRODUCTIVE ORGANS

Stamens:
*Number.*—About 40.
*Filament color.*—RHS Green-Yellow 1C.
Anthers:
*Length.*—2 mm.
*Shape.*—Club-like, basifixed.
*Color.*—RHS Yellow-Orange 17A.
*Pollen.*—Color: RHS Yellow-Orange 17A. Quantity: Little to none.
Pistil:
*Number.*—50.
*Length.*—8 mm.
*Style.*—Length: 7 mm. Color: RHS Green-Yellow 1C.
*Stigma.*—Shape: Rounded. Color: RHS Yellow 4C.
*Receptacle.*—Height: 1 cm. Diameter: 1 cm. Shape: Ovoid. Texture: Glabrous. Color: RHS Yellow-Green 143B.

OTHER CHARACTERISTICS

Seeds and fruits: None observed.
Disease/pest resistance: Tolerant of powdery mildew (*Podosphaera pannosa*) and blackspot (*Diplocarpon rosaea*).
Temperature tolerance: Observed tolerance between −25° C. to at least 40° C. degrees.

What is claimed is:

1. A new and distinct cultivar of *Rosa* plant named 'BOZFRA021' as herein illustrated and described.

* * * * *